(12) United States Patent
Braido

(10) Patent No.: US 10,058,422 B2
(45) Date of Patent: Aug. 28, 2018

(54) TRANSCATHETER VALVE STENT ANCHORS

(71) Applicant: St. Jude Medical, LLC, Abbott Park, IL (US)

(72) Inventor: Peter N. Braido, Wyoming, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 0 days.

(21) Appl. No.: 15/423,807

(22) Filed: Feb. 3, 2017

(65) Prior Publication Data

US 2017/0143484 A1    May 25, 2017

Related U.S. Application Data

(63) Continuation of application No. 14/164,611, filed on Jan. 27, 2014, now Pat. No. 9,597,180.

(60) Provisional application No. 61/766,783, filed on Feb. 20, 2013.

(51) Int. Cl.
*A61F 2/06* (2013.01)
*A61F 2/24* (2006.01)

(52) U.S. Cl.
CPC .......... *A61F 2/2418* (2013.01); *A61F 2/2436* (2013.01); *A61F 2220/0008* (2013.01); *A61F 2230/005* (2013.01); *A61F 2230/0013* (2013.01); *A61F 2230/0054* (2013.01)

(58) Field of Classification Search
CPC .... A61F 2/2418; A61F 2/2409; A61F 2/2412; A61F 1120/0054; A62F 2220/0016
See application file for complete search history.

(56) References Cited

U.S. PATENT DOCUMENTS

| | | |
|---|---|---|
| D660,967 S | 5/2012 | Braido et al. |
| 2007/0112423 A1* | 5/2007 | Chu ............ A61B 17/064 623/2.11 |
| 2007/0173929 A1* | 7/2007 | Boucher ............ A61F 2/07 623/1.35 |
| 2007/0255395 A1 | 11/2007 | Pollock et al. |
| 2011/0098800 A1 | 4/2011 | Braido et al. |
| 2011/0098802 A1 | 4/2011 | Braido et al. |
| 2012/0046741 A1* | 2/2012 | Tuval ............ A61F 2/2418 623/2.18 |
| 2012/0053681 A1 | 3/2012 | Alkhatib et al. |

* cited by examiner

*Primary Examiner* — Thomas J Sweet
*Assistant Examiner* — Tiffany Shipmon
(74) *Attorney, Agent, or Firm* — Lerner, David, Littenberg, Krumholz & Mentlik, LLP

(57) ABSTRACT

A stent for use in a prosthetic heart valve has a plurality of expandable and collapsible closed cells, a portion of which form an annulus section adapted for placement within the annulus of the native heart valve. Anchor features of the stent residing within at least some closed cells are adapted to engage tissue of the heart, including native valve leaflets, the sinotubular junction, or another implanted device when the prosthetic valve is implanted in the heart. The anchor features may help to retain the prosthetic valve in position, without interfering with the opening and closing of the valve leaflets. Furthermore, the anchor features may be configured to allow the stent to be resheathed into a delivery device after the portion of the stent with the anchor feature has expanded out of the delivery device.

22 Claims, 9 Drawing Sheets

TRANSCATHETER VALVE STENT ANCHORS

CROSS-REFERENCE TO RELATED APPLICATIONS

The present application is a continuation of U.S. patent application Ser. No. 14/164,611, filed Jan. 27, 2014, which claims the benefit of the filing date of U.S. Provisional Patent Application No. 61/766,783 filed Feb. 20, 2013, the disclosures of which are both hereby incorporated by reference herein.

FIELD OF THE INVENTION

The present invention is directed to prosthetic heart valves for replacement of native heart valves, to stents for use in such prosthetic heart valves, and to methods of treating patients with such prosthetic heart valves.

BACKGROUND OF THE INVENTION

Certain prosthetic heart valves incorporate an expandable stent body and valve elements such as prosthetic valve leaflets mounted to the stent body. Valves of this type may be implanted in the heart by advancing the valve into the body of the patient with the stent body in a collapsed condition in which the stent body has a relatively small diameter. Once the valve is positioned at the desired implantation site, the stent body is brought to an expanded condition in which the stent body bears on the surrounding native tissue and holds the valve in place. The valve acts as a functional replacement for the diseased native valve. Thus, the valve elements inside the stent body permit blood flow in the antegrade direction but substantially block flow in the opposite, retrograde direction. For example, a prosthetic valve may be advanced to a site within a diseased native aortic valve percutaneously through the arterial system and into the aorta to the native aortic valve. In a transapical placement, a prosthetic valve may be advanced through an incision in the apex of the heart and through the left ventricle to the native aortic valve. Other approaches through other access sites can be used. Once the prosthetic valve is in place, it permits flow from the left ventricle into the aorta when the left ventricle contracts during systole, but substantially blocks retrograde flow from the aorta into the left ventricle during diastole.

There are significant challenges in the design of an expandable stent body and valve. For example, the stent body desirably can be collapsed to a relatively small diameter to facilitate advancement into the body. However, the stent body must be capable of expanding to an operative, expanded condition in which the stent body securely engages the surrounding native tissues to hold the valve in place. The valve should form a good seal with the surrounding native tissues to prevent leakage around the outside of the prosthetic valve, commonly referred to as perivalvular leakage. The stent body, in its expanded, operative condition, desirably does not apply excessive forces to the annulus of the native valve. Excessive forces on the annulus of the native aortic valve can disrupt the electrical conduction system of the heart and also can impair the functioning of the mitral valve. These issues are complicated by the fact that the native valve leaflets ordinarily are left in place when an expandable prosthetic valve is implanted. The diseased native valve leaflets and other diseased tissues may present an implantation site which is irregular. For example, patients with calcified or stenotic aortic valves may not be treated well with the current collapsible valve designs, and may encounter problems such as (1) perivalvular leakage (PV leak), (2) valve migration, (3) mitral valve impingement, (4) conduction system disruption, etc., all of which can lead to adverse clinical outcomes. To reduce these adverse events, the optimal valve would seal and anchor adequately without the need for excessive radial force that could harm nearby anatomy and physiology.

As the patient population becomes younger with less tissue calcification, the use range of prosthetic heart valves expands to larger sizes and thus greater forces. Additionally, younger patients may be more likely to require bicuspid valve replacements and may have larger, more diseased, and more elliptically shaped aortic valves. Stent designs without an aortic section, as well as stents that need to anchor in the aorta, will need to anchor and support post deflection of the valve as it pulls inward from pressure closing the valve. If a valve is not designed to function in these environments, it may result in several types of adverse events described above since distortion of the valve can result in the loss of valve coaptation, loss of valve apposition, and overall higher stresses. In these environments, anchoring will become even more important to ensure valve coaptation in most all configurations with a reduction of high stresses in the critical areas of the prosthesis while maintaining valve apposition with native anatomy.

Numerous prosthetic valve and stent body designs have been proposed. However, despite all of the attention devoted to such designs, still further improvements would be desirable.

BRIEF SUMMARY OF THE INVENTION

A stent for use with a prosthetic heart valve for replacement of a native heart valve comprises an expandable stent body having a collapsed configuration and an expanded configuration. The stent body includes a plurality of closed cells and at least one anchor feature formed integrally with the stent. Each anchor feature resides within a closed cell of the stent and has an engagement portion adapted to engage a surface in a heart.

The engagement portion can be configured to engage any combination of a leaflet of the native heart valve, a portion of the sinotubular junction in the heart, and a portion of another device already implanted in the heart.

The stent is arranged in the collapsed configuration when received within a delivery sheath overlying the stent in a sheathed position, and the stent is arranged in the expanded configuration when the sheath is not overlying the stent in an unsheathed position. The anchor feature is oriented at an oblique angle to a longitudinal axis of the delivery sheath so that the stent may be resheathed when the sheath is in a position between the sheathed position and the unsheathed position. The anchor feature slopes radially outwardly from the stent when the stent is in the expanded configuration, and the anchor feature extends axially when the stent is in the collapsed configuration.

The engagement portion of the anchor feature can include an anchor tip with a first end connected to the stent, a second end connected to the stent, and an intermediate portion between the first and second ends. The intermediate portion of the anchor tip can include a single piece that is acute or blunted. The intermediate portion of the anchor tip can alternately include multiple separate pieces. These separate pieces can include different configurations, such as blunted ends.

The stent can include a first annular row of cells connected to a second annular row of cells by at least one connector. The anchor feature is connected to the connector. The connector can be a commissure attachment feature. The anchor features can be connected on one or both sides to the connectors or commissure attachment features. The anchor features can be connected to the stent at a connector, proximal of the connector, or distally of the connector. Two or more anchor features can be connected on each side to the same connector or commissure attachment features for a nested anchor feature configuration.

The engagement portion of the anchor feature can flare distally from the stent or proximally from the stent. A stent can include two anchor features with engagement portions, with the engagement portion of one anchor feature flaring distally from the stent and the engagement portion of one anchor feature flaring proximally from the stent.

The latch members can include a variety of materials. These include animal tissues, such as porcine, ovine and bovine pericardium or porcine sub-mucosa. These materials also include fabrics, such as knit or woven polyester and non-woven fabrics. These materials can further include collagen and water-absorbing polymers such as poly(acrylic acid). The materials can still further include biocompatible adhesives such as epoxy amines. Still further, these materials can include bio-absorbable materials such as polyglactin, copolymers of lactide and caprolactone, and polylactides.

DETAILED DESCRIPTION

While the present invention will be described more fully hereinafter with reference to the accompanying drawings, in which particular embodiments of stents and methods of delivery are shown, it is to be understood at the outset that persons skilled in the art may modify the invention herein described while achieving the functions and results of this invention. Accordingly, the descriptions that follow are to be understood as illustrative and exemplary of specific structures, aspects and features within the broad scope of the present invention and not as limiting of such broad scope. Like numbers refer to similar features of like elements throughout.

Figure 1:
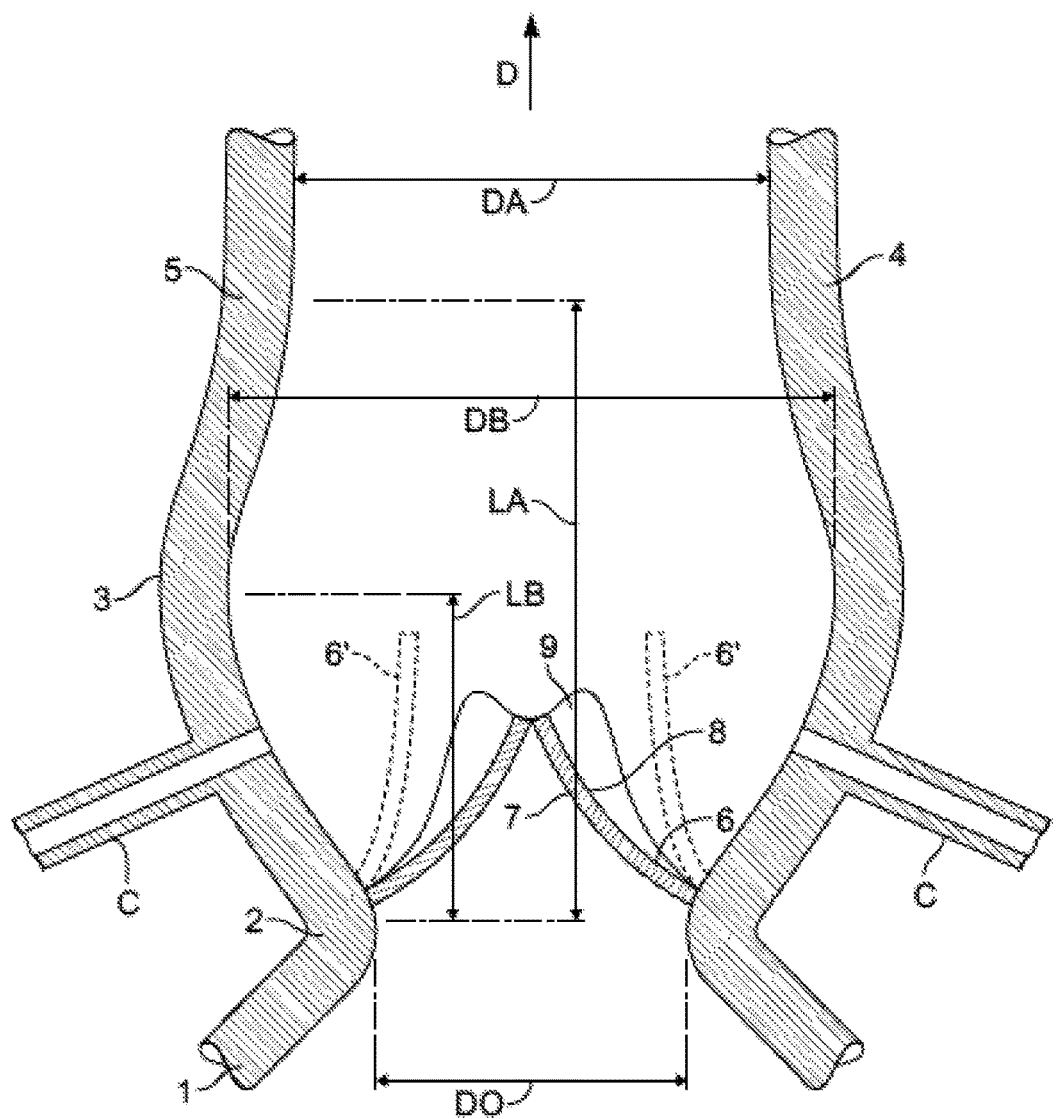
FIG. 1 is a schematic sectional view of the aortic root tissue in a typical human heart.

FIG. 1 is a simplified view of the geometry or anatomy of the aortic root tissue in a typical human heart. The left ventricular outflow tract (LVOT) 1 communicates with the ascending aorta 5 through the annulus 2 of the native aortic valve and the Valsalva sinus 3. The sinus joins the aorta at the sinotubular junction (STJ) 4. The native aortic valve typically includes three native valve leaflets 6, of which only two are visible in FIG. 1. As the left ventricle contracts during systole, blood is forced from the LVOT 1 through the native valve and sinus and into the aorta 5, moving generally in the downstream or antegrade flow direction indicated by arrow D. In a healthy individual, the native valve leaflets 6 open away from one another and move to the position schematically shown in broken lines at 6' to permit flow in this direction. During diastole, when the ventricle is not contracting, the native valve leaflets 6 move back to the position indicated in solid lines in FIG. 1, where they abut one another or "coapt" so as to substantially block flow in the upstream or retrograde direction, opposite to arrow D. The direction "distal" as used herein with reference to a feature of the native circulatory system refers to the direction of antegrade flow, i.e., the predominant direction of blood flow through such feature, as indicated by arrow D. The direction "proximal" as used herein with reference to a feature of the native circulatory system is the opposite direction.

The parameters identified in FIG. 1 are as follows: DO=orifice diameter, i.e., the interior diameter of native annulus 2; DA=the diameter of the aorta just distal to the sinus; DB=maximum projected sinus diameter (this sinus is sometimes known as the Valsalva sinus); LA=length of the sinus, i.e., the dimension in the distal direction from the annulus 2 to the sinotubular junction 4; and LB=distance in the distal direction between DO and DB.

The leaflets 6 have distal edges 9 remote from the annulus 2. Each native leaflet 6 has a surface 7, referred to herein as the "interior" surface of the leaflet, facing generally towards the other leaflets. Each native leaflet 6 also has a surface 8, referred to herein as the "exterior" surface of the leaflet, facing outwardly, away from the other leaflets and toward the wall of the sinus 3. The cross-sectional shape of such a native valve varies somewhat from individual to individual, and this variation can be increased by various types of disease. For example, disease can reshape the cross-section of a patient's valve to a circular, triangular, or elliptical shape, depending on the disease state.

Figure 2:
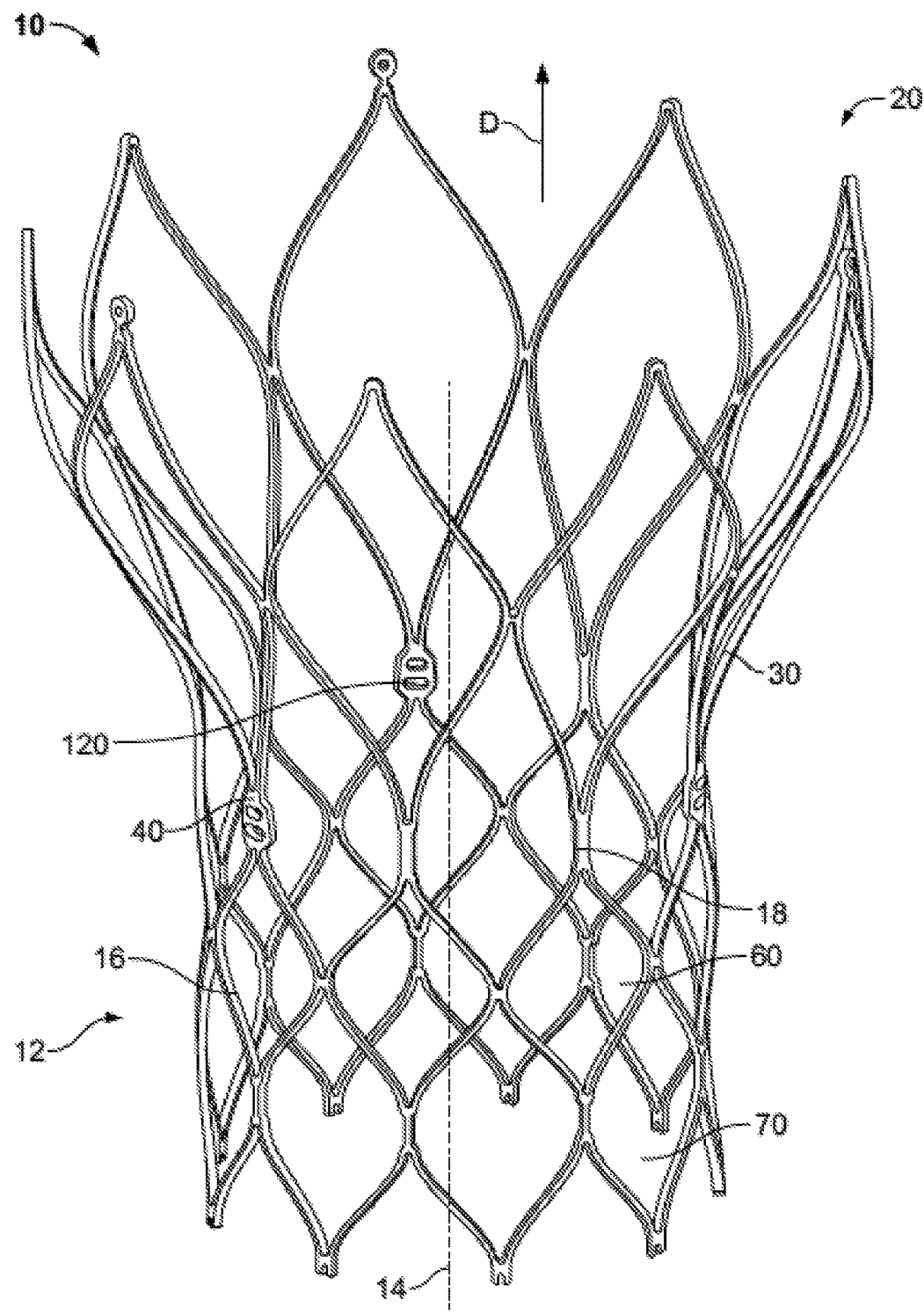
FIG. 2 is a perspective view of a prior art stent in an expanded configuration.

FIG. 2 shows a prior art collapsible stent for use with a prosthetic heart valve. Examples of collapsible prosthetic heart valves are described in U.S. Application Publication No. 2012/0053681 and U.S. Design Pat. No. D660,967, the entire contents of which are hereby incorporated by reference herein. An expandable stent body 10 is formed as a unitary structure as, for example, by laser cutting or etching a tube of a superelastic metal alloy such as a nickel-titanium alloy of the type sold under the designation NITINOL. Such a unitary structure can also be referred to as a "non-woven" structure, in that it is not formed by weaving or winding one or more filaments. In its fully-expanded, unconstrained configuration, the illustrated embodiment of stent body 10 includes an annulus section 12, an aorta section 20 and support struts 30 extending between the annulus section and the aorta section. The annulus section 12 in the expanded configuration is generally in the form of a cylindrical tube having a central axis 14, whereas aorta section 20 is generally in the form of a hoop coaxial with the annulus section. The annulus section 12 can be in the form of other shapes, such as elliptical or triangular, depending on the patient's anatomy. Not all embodiments of stent body 10 include an aorta section 20. For example, stents for aortic valves, as well as stents for bicuspid and/or mitral valves may not include an aorta section 20.

The stent body 10 is adapted for installation in the body of a patient with the annulus section 12 adjacent the annulus 2 and with the aorta section 20 adjacent the sinotubular junction 4 and aorta 5. Thus, when the valve incorporating the stent body 10 is placed in the patient, the aorta section 20 will be disposed distal to the annulus section 12 in the frame of reference of the patient's circulatory system. Accordingly, as used with reference to features of the stent body and valve, the direction D (FIGS. 1 and 2) along axis 14 from the annulus section 12 towards the aorta section 20 is referred to as the distal direction, and the opposite direction is taken as the proximal direction. Stated another way, the distal direction along the stent body is the direction from the end of the stent which is intended for disposition at a proximal location in the frame of reference of the circulatory system to the end of the stent which is intended for disposition at a more distal location in the frame of reference of the circulatory system. Also, the outward direction as used with reference to the stent body is the direction away from the proximal-to-distal axis 14. The directions toward and away from axis 14 are also referred to herein as the "radial" directions. As used with reference to features of the stent body, the "circumferential" directions are the directions around axis 14.

As best seen in FIG. 2, the annulus section 12 includes numerous cells defined by interconnecting struts 16 which join one another at intersection points. These cells are disposed in a proximal row 70 and distal row 60, each such row extending circumferentially around the proximal-to-distal axis 14 so that the cells cooperatively form a generally cylindrical wall. In the expanded condition, the struts 16 of each cell form a generally diamond-shaped structure. In the unexpanded or collapsed configuration, the struts 16 of each cell extend substantially proximally and distally, so that each cell is collapsed in the circumferential direction. The intersection points 18 between the struts 16 on the distal side of distal row 60 define the distal edge of the annulus section 12. These intersection points are referred to herein as the distal crests 18 of the annulus section 12.

The annulus section 12 also includes a set of commissure features 40 formed integrally with the remainder of the stent body. The commissure features 40 are found at three locations spaced equally around the circumference of the annulus section. Each commissure feature 40 may include one or more eyelets 120 therein. Three prosthetic valve leaflets (not shown) are sutured to the commissure features 40, so that the leaflets are disposed within the annulus section 12 of the stent body. The sutures (not shown) may extend through eyelets 120. A lining or "cuff" (not shown) may be provided on the interior surface, exterior surface or both of the annulus section 12, over all or part of the axial extent of the annulus section 12. The leaflets and cuff may be formed from conventional biocompatible materials such as synthetic polymers and animal tissues such as pericardial tissues. Stent body 10 can include more than three or fewer than three commissure features 40, for example to accommodate more or fewer than three valve leaflets.

Aorta section 20 is formed by a set of struts 16 which define a row of half-cells. The configuration of the struts 16 in aorta section 20 may be varied from that shown. For example, the aorta section 20 may include one or more rows of full cells such as those constituting the annulus section 12. Also, the support struts 16 may have a branched configuration, so that the distal end of each support strut is connected to plural points in the aorta section 20. More or fewer support struts 16 may be provided.

Figure 3:
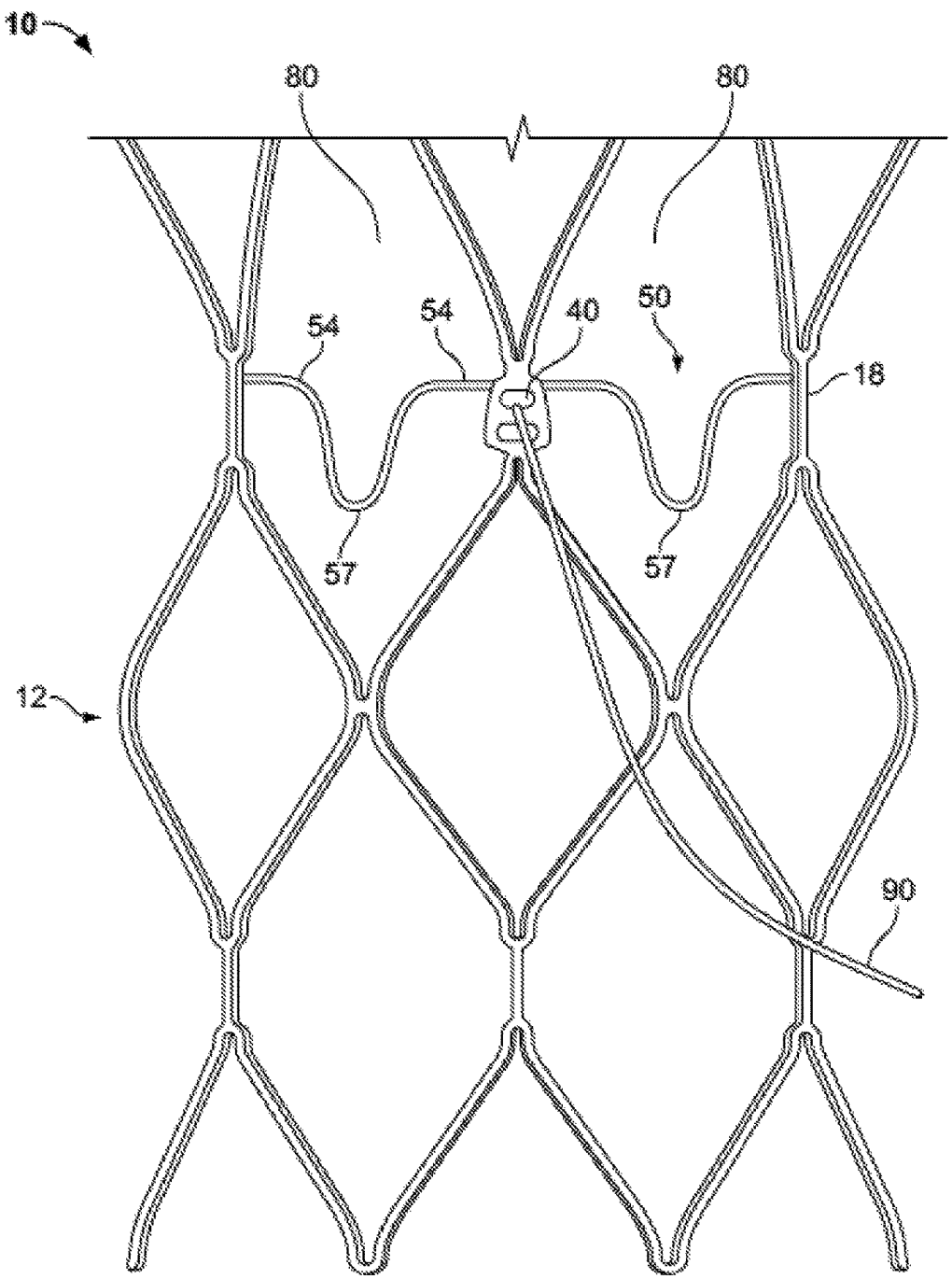
FIG. 3 is an enlarged elevational view of a portion of a stent with anchor features residing within closed cells of the stent.

In one embodiment of the invention, best seen in FIG. 3, the stent body 10 also includes anchor features in the nature of latch members 50. The latch members 50 are equally spaced from one another in the circumferential direction and reside within adjacent closed cells 80. More specifically, the latch members 50 reside within the space of the distal crests 18 and commissure features 40 of the annulus section 12 and above the level of the leaflet belly 90 of the valve leaflet. The locations of the latch members 50 allow the stent body 10 to maintain a similar or identical crimp profile as the stent body 10 would have in the absence of the latch members 50. Alternatively, the locations of the latch members 50 can be higher than the free edge of the prosthetic leaflet (not shown) to avoid contact between the prosthetic leaflet and the latch members 50 during crimping or other use. Although the highly schematic embodiment illustrated in FIG. 3 has three latch members 50 (two of which can be seen in the highly schematic view) equally distanced around the circumference of the stent body 10, the number and location of latch members 50 is a matter of design choice. For example, alternate embodiments of a stent could include a single latch member 50 or two or more latch members. The latch members 50 could also be spaced unequally around the circumference of the stent body 10. For example, for a stent to be used with a bicuspid valve, it may be preferable to include only two latch members 50 (i.e., one latch member per leaflet). Depending on the specific anatomy of the heart valve and native leaflets into which the stent will be implanted, spacing between latch members 50 other than equal spacing may be preferred. Further, the number of latch members 50 does not necessarily need to correspond to the number of leaflets in the valve into which the stent is being deployed. For example, it may only be desired to utilize two latch members 50 in a tricuspid valve. In this scenario, two valve leaflets would be engaged by latch members with the remaining leaflet unengaged by any latch member. Additionally, latch members 50 do not need to reside in adjacent cells 80. Rather, one or more empty cells 80 (i.e. cells without latch members 50) could reside between cells with latch members.

The latch members 50 are connected on each side to either a distal crest 18 or commissure feature 40. Each latch member 50 includes a pair of connection struts 54. Similar to the remainder of stent body 10, the connection struts 54 are elongated solid members formed of a superelastic metal alloy such as a nickel-titanium alloy and can be of any cross sectional shape such as circular or oval. The connection struts 54 can be formed of other materials, or additional materials, such as polymers, bio-absorbable materials, drug eluting materials, or fabric coatings to enhance tissues in-growth. These and other materials are discussed more completely below. Each connection strut 54 connects to either a distal crest 18 or a commissure feature 40. Each latch member 50 also includes a generally U- or V-shaped intermediate global portion 57 joined between connection struts 54. The latch members 50, including connection struts 54 and intermediate global portion 57, can be formed integrally with the remainder of stent body 10. For example, a single tube of a superelastic metal alloy can be laser cut or etched, forming the entire stent body 10, including the latch members 50, from the original single tube. Alternatively, the latch members 50 can be formed separately from the stent body 10 and can later be connected to the stent body, for example by welding, suturing, gluing or other methods.

In the expanded configuration of the stent body 10, U-shaped portion 57 slopes radially outwardly so as to be disposed radially outward of the distal end of annulus section 12. The U-shaped portion 57 lies at the distal end of the annulus section 12.

The structure of the latch member 50 allows it to collapse in the radial direction. Thus, in the collapsed configuration of the stent body 10, the connection struts 54 and U-shaped portion 57 extend substantially axially.

Figure 4:
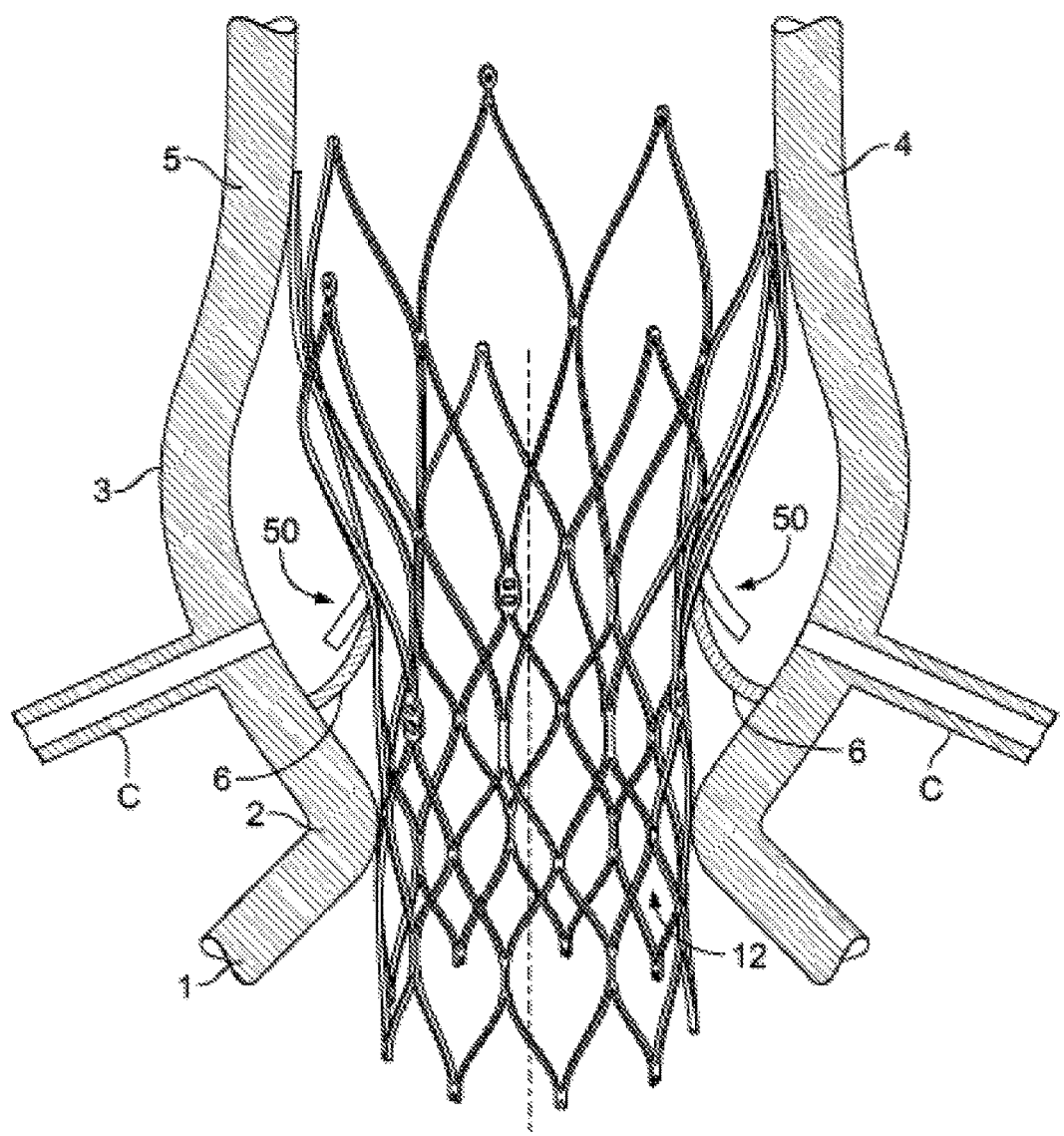
FIG. 4 is a schematic of a stent, according to an embodiment of the invention, deployed in a human heart.

In operation, the valve is brought to a collapsed condition and mounted on a delivery device (not shown) such as an elongated probe having a sheath adapted to retain the stent body in the collapsed condition, and having provisions for moving the sheath relative to the stent body to release the stent body from the sheath. The delivery device is advanced into the patient's body until the valve is aligned with the native aortic valve, with the annulus section 12 adjacent the annulus 2 of the aorta. The valve is released from the sheath and stent body 10 expands under its own resilience. The resilient expansion may occur solely as a result of release of mechanical constraint of the stent body, or may include expansion resulting from the effects of temperature change on the material of the stent body. Preferably, the entire expansion of the stent body from its collapsed condition to its expanded, operative condition is brought about by the stent body itself. Stated another way, the stent body desirably is fully self-expanding and does not require a balloon or mechanical movement device to bring about any part of the expansion. Referring to FIGS. 1 and 4, the annulus section 12 engages the annulus 2 of the native aortic valve, and also engages the interior surfaces 7 of the native valve leaflets 6. Each latch member 50 engages one of the native valve leaflets 6 at or near the distal edge 9 of such native leaflet. The U-shaped portion 57 (not labeled in FIG. 4) of each latch member 50 upon expansion bears on the exterior surface 8 of the leaflet 6 at or near the distal edge. In other words, the native valve leaflets 6 are clamped between the latch members 50 and the remainder of the stent body 10. It should be appreciated that the leaflets 6 typically have irregular shapes. For example, the leaflets 6 may be nodular or rough. The aorta section 20 engages the native anatomy at or near the sinotubular junction 4.

Although the stent reaches an expanded configuration, it typically does not reach its fully-expanded, unconstrained configuration. Thus, the resilience of the stent body normally causes the aortic section 20 to bear on the sinotubular junction 4 and also causes the annulus section 12 to bear on the annulus 2 and on the interior surfaces of the leaflets. The prosthetic valve leaflets open to allow distal or antegrade flow of blood during systole, and close to block proximal or retrograde flow during diastole. The engagement of the latch members 50 with the native valve leaflets 6 helps to maintain the stent body 10, and hence the valve, in position. In particular, such engagement helps to prevent movement of the valve in the proximal or retrograde direction. Therefore, the resilient engagement of the annulus section 12 and aorta section 20 with the native anatomy need not provide all of the force necessary to resist such movement. Moreover, the engagement of the latch members 50 with the native valve leaflets 6 tends to bias the native leaflets 6 inwardly toward the annulus section 12 of the stent body 10. This tends to improve sealing between the native leaflets 6 and the stent body 10 and helps to resist perivalvular leakage or retrograde flow around the outside of the stent body. The latch members 50 facilitate satisfactory valve action without the need for extremely high radial forces between the annulus section 12 of the stent body 10 and the native valve anatomy. This is advantageous, inasmuch as excessive radial forces on the native anatomy may disrupt the electrical conduction system of the heart and or distort the mitral valve, which is disposed near the annulus 2 of the aortic valve.

The latch members 50 may be altered in a variety of ways to further reduce PV leakage, especially near points of contact between the native leaflets 6 and the latch members 50. The latch members 50 can include materials such as animal tissues as, for example, porcine, ovine and bovine pericardium, porcine sub-mucosa, and synthetic fabrics such as knit or woven polyester, and non-woven fabrics. Collagen-impregnated fabrics may be used. Also, bio-absorbable materials such as polyglactin, copolymers of lactide and caprolactone, and polylactides can be used.

Latch members 50 covered in fabrics, for example, can promote tissue in-growth. As tissue grows into the fabric of the latch members 50, a better seal is created at the sites of the latch members 50, reducing the likelihood of PV leakage. Other alternatives to fabric that produce tissue in-growth at the site of the latch members 50 can also reduce PV leakage.

Latch members 50 alternatively can include a hygroscopic or sponge-like material that collapses easily and fills to a larger volume when the stent is expanded after implantation. This hygroscopic material, for example, can be a collagen foam or sponge similar to the material commercially available under the trademark Angioseal which is used to plug arteries, and to the similar material currently used for embolic protection.

In a further embodiment, material on the latch members 50 can be impregnated with a water-absorbing polymer. When allowed to expand as a result of implantation in a patient and consequent absorption of water from the patient's tissue and/or blood, these materials can fill any gaps between the latch members 50 and the native tissue to reduce PV leakage.

In still further embodiments, mechanical means, such as small coil or torsion springs, can be used as alternate or additional means to fill any gaps between the stent body 10 and the native tissue to reduce PV leakage. The mechanical means can be formed integrally with the stent body 10. For example, springs formed integrally with the stent body can project outwardly from the stent body 10 in the expanded condition, biasing the cuff outwardly toward the native tissue. Other mechanical means include coil springs that have a spring axis extending generally in a radially outward direction from the stent body 10. Such small coils and torsion springs are described more fully in U.S. Patent Application Publication No. 2011/0098802, the entire contents of which are hereby incorporated by reference herein.

The latch members 50 of the stent body 10 can be made to be bonded to native tissues as, for example, to native leaflets 6 during or after implantation. For example, a porcine pericardial strip on the latch members 50 can be used to bond a tissues-to-tissue joint. The bonding can be achieved, for example, by lower power lasers that minimize tissue vaporization, yet bond tissue together. Biocompatible adhesives, such as epoxy amines, have been applied in certain medical applications. Such adhesives can be applied around the perimeter of the latch members 50 to bond to native leaflets during or after implantation. These and other variants, as applied to a cuff of a prosthetic valve rather than latch members of a stent body, are described more fully in U.S. Patent Application Publication No. 2011/0098802.

The resilience of the latch members 50 allows them to attach to both calcified and non-calcified leaflets 6. For example, if a leaflet 6 is thick, nodular or both, the U-shaped portion 57 of the latch member 50 can be bent outwardly by the leaflet 6. In this condition, the latch member 50 tends to push the leaflet 6 inwardly against the annulus section 12 of the stent body 10. The systolic blood pressure tends to force the native valve leaflets 6 into engagement with the annulus section 12 of the stent body. By retaining the native leaflets 6 in position, the latch members 50 facilitate this action.

The prosthetic valve allows antegrade flow into the aorta, and also allows flow into the Valsalva sinus and thus into the coronary arteries C which communicate with the sinus. Engagement of the native valve leaflets 6 by the latch members 50 may help to assure that the native valve leaflets 6 do not block the openings of the coronary arteries.

Figure 5A:
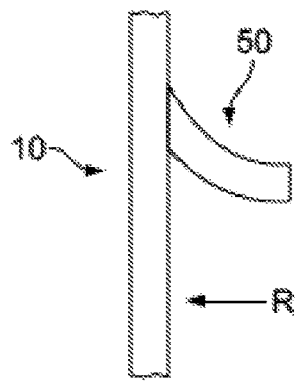
FIG. 5A is a highly schematic fragmentary side view depicting a portion of a stent incorporating an anchor feature according to an embodiment of the invention.

Various embodiments of latch members 50 can be used in conjunction with a stent having a closed cell design. FIG. 5A shows a side view of an embodiment of a latch member 50 along with the portion of the stent body 10 on which the latch member 50 is located. For simplicity of illustration, only a portion of the stent body 10 is depicted. The latch member 50 generally flares radially outward from the stent body 10 and also extends proximally from the points of attachment of the stent body 10 between distal crest 18 and commissure feature 40 (not visible in FIG. 5A). The location of the latch member 50 within the space between the distal crests 18 allows for the latch member 50 to be compressed radially inward in the direction of the arrow R shown in FIG. 5A. Additionally, the direction in which latch member 50 flares allows for the resheathability of the stent body 10. In the event that the proximal end of stent body 10 emerges from a deployment device (not shown) before the distal end of the stent body, the proximal end of the stent body will expand first while the distal end of the stent body remains within the deployment device. If repositioning becomes necessary, the direction in which latch member 50 flares will not hinder stent body 10 from being resheathed into the deployment device.

Figure 5B:
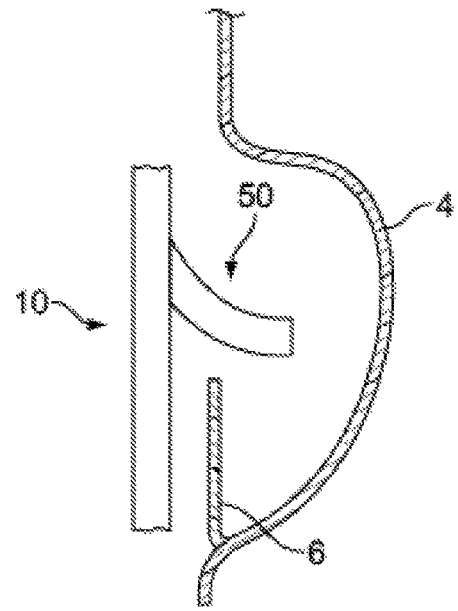
FIGS. 5B-5F are highly schematic fragmentary side views depicting portions of stents incorporating an anchor feature engaged with a heart or with an implanted device within a heart according to embodiments of the invention.
Figure 5C:
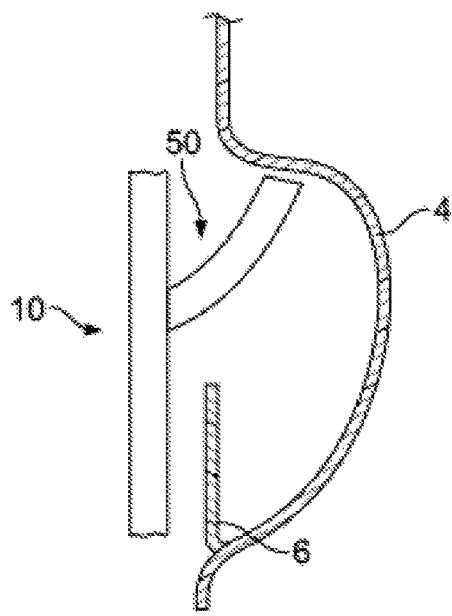

FIG. 5B shows the stent body 10 illustrated in FIG. 5A after it has been implanted into a patient. In this embodiment, the flared portion of latch member 50 engages a native leaflet 6 of the native heart valve. Referring now to FIGS. 5C-5F, there are shown side views of different embodiments of stent body 10 with latch members 50 implanted in the heart tissue of a patient. FIG. 5C shows an embodiment of stent body 10 with a latch member 50 that flares in substantially the opposite direction to that shown in FIG. 5B. In this embodiment, the latch member 50 flares distally from the stent body 10. This configuration allows the latch member 50 to primarily engage the tissue at the sinotubular junction 4. Engagement of the sinotubular junction 4 aids the stent in resisting migration in the distal direction. Additionally, the direction in which the latch member 50 flares allows resheathing of the stent if the distal end of stent body 10 is deployed from the delivery device (not shown) before the proximal end.

Figure 5D:
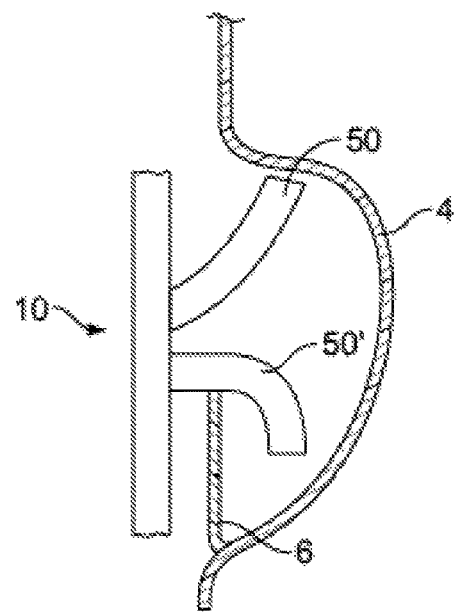

FIG. 5D shows another embodiment of stent body 10 with a pair of latch members 50, 50'. The distally flaring latch member 50 engages the sinotubular junction 4, while the proximally flaring latch member 50' simultaneously engages a leaflet 6 of the native heart valve. This configuration allows for added anchoring capability from the use of multiple latch members.

Figure 5E:
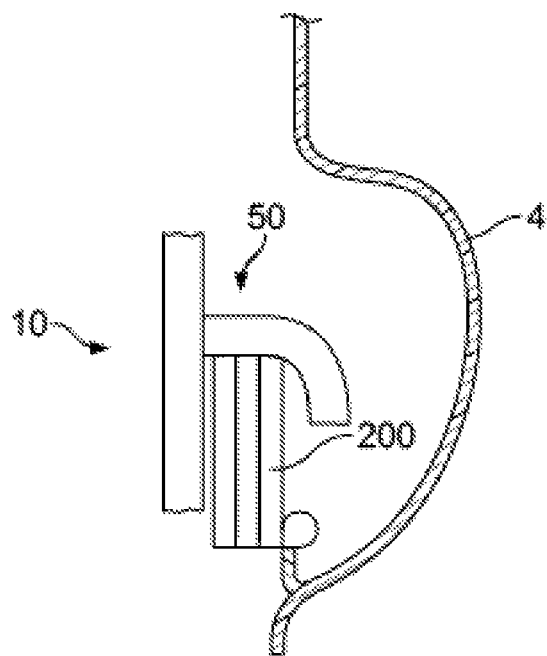
Figure 5F:
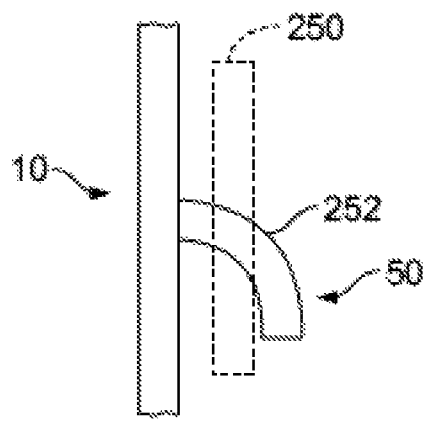

FIGS. 5E and 5F each show embodiments of stent body 10 with latch members 50 that do not primarily engage native heart tissue. In the embodiments shown in FIGS. 5E and 5F, the latch members 50 are similar to that shown in FIG. 5B in that the latch members flare outwardly in a proximal direction. However, in the embodiment shown in FIG. 5E, the latch member 50 engages a surgical valve 200 that has already been implanted in the patient rather than a native heart structure. In the embodiment shown in FIG. 5F, the latch member 50 engages stent features of another transcatheter aortic valve implant 250, such as between open cells 252 of the second implant. Latch members 50 can be designed to correspondingly mate to a device already implanted in the heart, such as surgical valve 200 or stent 250, depending on the specific features of the device already implanted in the heart. For example, if the surgical valve 200 is thicker than an average native leaflet, the latch member 50 could be designed to extend initially more radially outward to ensure that the latch member sufficiently engages or "hooks" the surgical valve, as seen in FIG. 5E. Similarly, for latch members 50 to engage cells of another stent 250, such as that shown in FIG. 5F, the latch members may extend farther or less far in the proximal or distal directions, may flare distally or proximally, or may extend at a more or less acute angle. The specific design of the latch members 50 will depend on the corresponding features of the already-implanted device. Also, as described above, the latch members 50 can be covered with any of a variety of materials. For latch members 50 that primarily engage other implanted devices, especially metal devices, it may be desirable to provide a fabric or other coating on the latch members to avoid metal-on-metal contact. In the absence of a coating on the latch members 50, the metal-on-metal contact could cause, for example, fretting corrosion, abrasion, or other types of corrosion or wear.

Figure 6A:
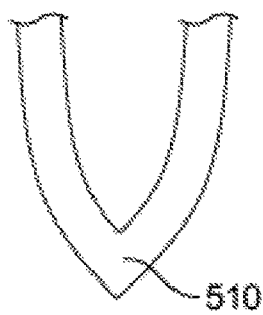
FIGS. 6A-6E are highly schematic fragmentary views depicting portions of stents according to further embodiments of the invention.
Figure 6B:
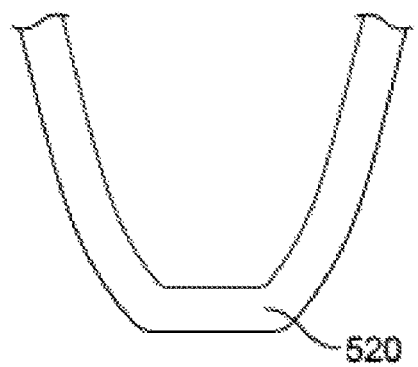
Figure 6C:
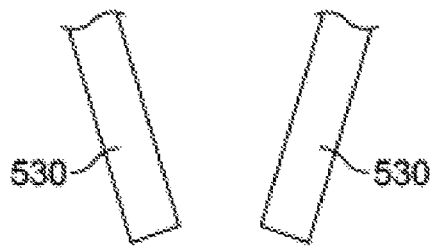
Figure 6D:
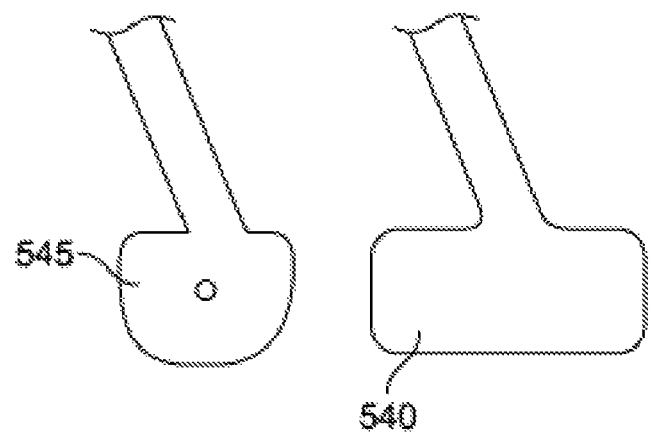
Figure 6E:
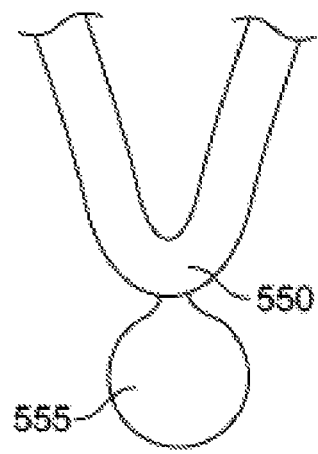

As mentioned above and shown in the embodiment illustrated in FIG. 3, the central portion 57 of the latch member 50 may be generally "U" shaped. Other shapes are within the scope of the invention and may be selected depending on the specific anatomy of the patient. Different embodiments of the central portion are illustrated in FIGS. 6A-6E. For example, FIG. 6A illustrates a central portion 510 with a very narrow or acute "V" shape. The central portion 520 of FIG. 6B is generally "U" shaped, but with a squared off or blunted tip. FIG. 6C shows a central portion that consists of two separate pieces 530, as opposed to the continuous central portions shown in FIGS. 6A-B. Other possible shapes of the central portion of latch member 50 include, but are not limited to, central portions with blunt piece 540 and a separate circular piece 545 as seen in FIG. 6D, and a central portion having a generally acute "V" shaped portion 550 with a blunt extension piece 555 as shown in FIG. 6E.

The choice of a particular shape for the central portion of latch member 50 may be based on a number of factors, such as particular types of trauma existing in the patient's heart tissue, the need for resheathability of the stent, and the specific type of interface with which the latch member central portion will engage. For example, a latch member 50 having an acute "V"-shaped central portion 510 would apply relatively high force at the point of engagement. However, if a particular patient would be at a high risk of having his cardiac tissue pierced by such relatively high force, a blunted central portion 520 might be more appropriate as it would distribute the applied forces across a larger area. In patients with nodules of calcification on their native heart valves, for instance, the central portion with separate pieces 530 may provide the greatest flexibility for optimal engagement of the latch member to the site of engagement. Similarly, the latch member with separate blunt pieces 540 and 545 shown in FIG. 6D could provide greater flexibility for maintaining contact with irregular surfaces and still provide a relatively large area over which the contact forces may be distributed. When engaging a previously existing implant, such as another transcatheter aortic valve implant, the latch member central portion may be shaped to enhance engagement capabilities based on the specific shape of the previously existing implant.

Although specific embodiments of latch members 50 have been described, other sizes and shapes are within the scope of the invention. For example, latch members 50 with larger or smaller cross sections may be used to provide different levels of resilience. Further, shapes not discussed above may been implemented, for example, to match the condition of the patient's native valve leaflets 6 as measured, for example, by imaging techniques before or during the procedure. A kit including different valves with stent bodies having different latch members may be provided to facilitate such selection.

Figure 7:
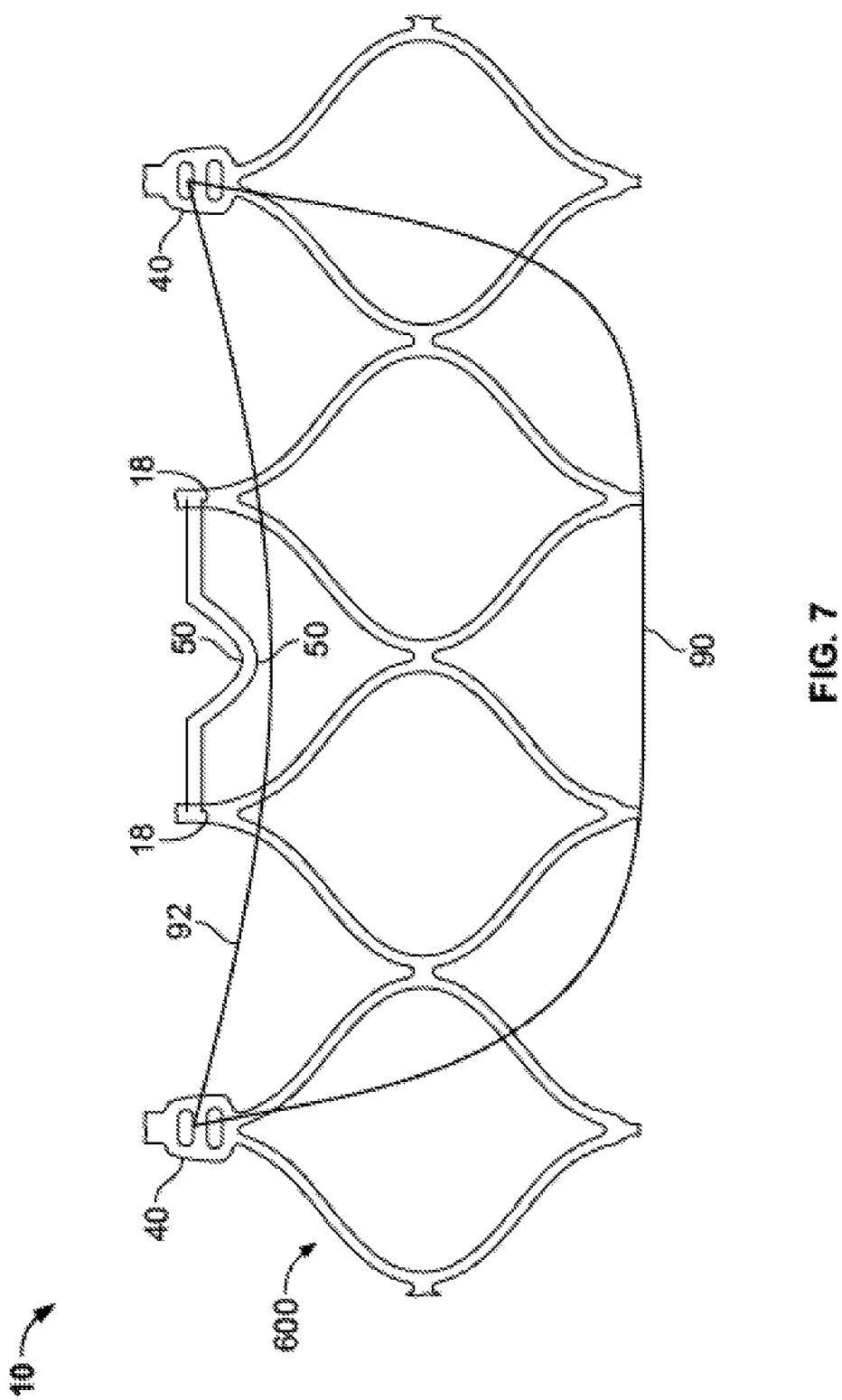
FIG. 7 is a fragmentary elevational view of a portion of a stent according to an embodiment of the invention with a portion of an attached valve leaflet, and with certain features omitted for clarity of illustration.

FIG. 7 shows a continuous run of stent cells 600 within a portion of stent body 10 to illustrate, but not limit, different attachment locations of the latch members 50. For example, the latch members 50 may be attached at one end to a commissure attachment feature 40 to which a valve leaflet 90 may also be attached, or above or below such commissure feature, and at the other end to a distal crest 18 (this configuration not shown in FIG. 7). The latch members 50 may also be attached at both ends to the distal crests 18, or above or below such distal crests. Additionally, multiple connections per distal crest 18 or commissure attachment feature 40 are possible to create nested latch members 50 within a single cell, as illustrated in FIG. 7. Preferably, the connections are made far enough distally of the leaflet belly 90 and the free edge 92 of the leaflet to avoid contact between the latch members 50 and the leaflets as the leaflets open and close and as the stent body 10 is crimped or expanded.

Numerous other variations and combinations of the features described above may be employed. For example, features described in one or more embodiments may be combined with the features described in other embodiments. The cellular structure of the stents described above may also be varied. For example, the features described above may be employed in woven stent bodies and in stent bodies which are not fully self-expanding as, for example, stent bodies which are forcibly expanded by a balloon or mechanical device during implantation.

Although the foregoing most frequently refers to prosthetic aortic valves, it will be appreciated that prosthetic valves in accordance with this invention may be used for other cardiac valves. As just one example of this, elliptical prosthetic valves in accordance with the invention may be used as prosthetic mitral valves.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of implanting a prosthetic heart valve comprising:

positioning a prosthetic heart valve in a collapsed condition within a sheath of a delivery device, the prosthetic heart valve including a stent having (i) a plurality of struts forming cells and (ii) an anchor feature with a first end coupled to a first portion of one of the cells and a second end coupled to a second portion of the one of the cells;

advancing a sheath of a delivery device to a patient's native valve, the sheath retaining the prosthetic heart valve in the collapsed condition so that (i) no portion of the anchor feature overlaps in a radial direction of the stent with any of the plurality of struts forming the cells and (ii) the first end and the second end of the anchor feature are spaced apart by a first distance;

releasing the prosthetic heart valve from the sheath;

transitioning the prosthetic heart valve from the collapsed condition to an expanded condition so that the first end and the second end of the anchor feature are spaced apart by a second distance greater than the first distance;

engaging the anchor feature to a surface of a heart of the patient; and releasing the prosthetic heart valve from the delivery device.

2. The method of claim 1, wherein the step of engaging the anchor feature to a surface of the heart includes engaging the anchor feature to at least one of a portion of a leaflet of the native valve or a portion of a sinotubular junction of the heart.

3. The method of claim 1, wherein after the step of engaging the anchor feature to the surface of the heart and prior to releasing the prosthetic heart valve from the delivery device, the anchor feature is oriented at an oblique angle to a longitudinal axis of the sheath so that the stent may be resheathed.

4. The method of claim 3, wherein the anchor feature slopes radially outwardly from the stent when the stent is in the expanded condition.

5. The method of claim 3, wherein the anchor feature is parallel to a longitudinal axis of the stent when the stent is in the collapsed condition.

6. The method of claim 1, wherein the step of engaging the anchor feature to a surface of a heart of the patient includes simultaneously engaging both a portion of a leaflet of the native valve and a portion of a sinotubular junction of the heart.

7. The method of claim 1, wherein the step of engaging the anchor feature to a surface of a heart of the patient includes engaging the anchor feature to a device implanted in the patient's heart.

8. The method of claim 1, wherein the anchor feature includes an anchor tip between the first end and the second end.

9. The method of claim 8, wherein the anchor tip has a sharp "V" shape.

10. The method of claim 8, wherein the anchor tip is blunted.

11. The method of claim 8, wherein the anchor tip includes at least two separate pieces.

12. The method of claim 11, wherein at least one of the at least two separate pieces includes a blunted end.

13. The method of claim 1, wherein the cells of the stent include a first annular row of cells connected to a second annular row of cells by at least one connector, the anchor feature being coupled to the at least one connector.

14. The method of claim 13, wherein the at least one connector is a commissure attachment feature.

15. The method of claim 14, wherein at least two anchor features are each coupled at the first end of the anchor feature to a first connector and are each coupled at the second end of the anchor feature to a second connector to form a nested anchor feature configuration.

16. The method of claim 1, wherein the cells of the stent include a first annular row of cells connected to a second annular row of cells by at least one connector, the first end of the anchor feature being coupled to the stent body between an inflow end of the stent and the at least one connector.

17. The method of claim 1, wherein stent cells include a first annular row of cells connected to a second annular row of cells by at least one connector, the first end of the anchor feature being coupled to the stent between an outflow end of the stent and the at least one connector.

18. The method of claim 1, wherein after the step of engaging the anchor feature to the surface of a heart of the patient, an engagement portion of the anchor feature flares toward an outflow end of the stent.

19. The method of claim 1, wherein after the step of engaging the anchor feature to the surface of the heart of the patient, an engagement portion of the anchor feature flares toward an inflow end of the stent.

20. The method of claim 1, wherein the anchor feature includes a first anchor feature and a second anchor feature, and after the step of engaging the anchor feature to the surface of the heart of the patient, an engagement portion of the first anchor feature flares toward an inflow end of the stent and an engagement portion of the second anchor feature flares toward an outflow end of the stent.

21. The method of claim 1, wherein the anchor feature spans circumferentially across the one cell.

22. The method of claim 1, wherein in the expanded condition of the heart valve, no portion of the anchor feature is positioned radially inward of the one cell.

* * * * *